US00PP23196P3

(12) United States Plant Patent
Maillard et al.

(10) Patent No.: US PP23,196 P3
(45) Date of Patent: Nov. 20, 2012

(54) PEACH TREE NAMED 'SWEETREGAL'

(50) Latin Name: *Prunus persica L. Batsch*
Varietal Denomination: SWEETREGAL

(75) Inventors: Arsene Maillard, Elne (FR); Laurence Maillard, Elne (FR)

(73) Assignee: Agro Selections Fruits, Elne (FR)

( * ) Notice: Subject to any disclaimer, the term of this patent is extended or adjusted under 35 U.S.C. 154(b) by 0 days.

(21) Appl. No.: 13/064,022

(22) Filed: Mar. 2, 2011

(65) Prior Publication Data

US 2011/0219492 P1 Sep. 8, 2011

(30) Foreign Application Priority Data

Mar. 2, 2010 (QZ) ..... PBR 20100499

(51) Int. Cl.
*A01H 5/00* (2006.01)

(52) U.S. Cl. ..... Plt./195

(58) Field of Classification Search ..... Plt./195
See application file for complete search history.

*Primary Examiner* — Annette Para

(74) *Attorney, Agent, or Firm* — Westerman, Hattori, Daniels & Adrian, LLP

(57) ABSTRACT

A new and distinct variety of white peach tree, denominated 'SWEETREGAL', has a large fruit of very long shelf life without alteration after harvesting, a semi-sweet white flesh of high eating quality and an attractive bright purple red skin color on a washed-pink red ground. The tree is of large size and is vigorous. Fruit can be consumed crunchy or at maturity.

3 Drawing Sheets

Latin name of the genus and species of the plant claimed: *Prunus persica L. Batsch.*

Variety denomination: 'SWEETREGAL'.

This application claims priority of Community plant variety right No. 2010/0499 filed on Mar. 2, 2010 which is hereby incorporated by reference in its entirety.

BACKGROUND OF THE NEW VARIETY

The present invention relates to a new and distinct variety of white peach tree, *Prunus persica L. Batsch*, which has been given the variety denomination 'SWEETREGAL'. This new tree produces fruit with a long shelf life without alteration both on the tree after growth completion and after harvesting, large fruit with very good eating quality, fresh fruit for fresh market in early August in the Pyrénées-Orientales department, France. Contrast is made to 'MASNOW' (non-patented), 'SWEETLOVE' (U.S. Plant Pat. No. 21,144) peach trees, standard varieties, for reliable description. 'SWEETREGAL' is a promising candidate for commercial success in that it has a semi-late period flowering, fruit with very long shelf life without alteration after harvesting, and so a very durable fruit.

ORIGIN OF THE VARIETY

'SWEETREGAL' peach tree originated in a cultivated area of the south of France, in the Pyrénées-Orientales department, where it was tested. The male parent is 'NECTACHIEF' (U.S. Plant Pat. No. 19,330), yellow nectarine tree with a very attractive fruit of a round shape and a bright red blush color. The female parent 'MALATEWHITE' (non-patented) is a white peach tree with a well-balanced flavor. 'NECTACHIEF' (U.S. Plant Pat. No. 19,330) was obtained by seedling. The male parent is 'ZAITABO' nectarine tree (sold under the trademark BIG TOP®) and the female parent is 'ARMKING' (U.S. Plant Pat. No. 2,943) nectarine tree. 'NECTACHIEF' (U.S. Plant Pat. No. 19,330) blooms in March in South of France. More particularly, 'NECTACHIEF' blooms at the same time as 'NECTAROSS' or 'MAILLARMATE', and 3 days after 'ZAITABO' (BIG TOP®) between the $7^{th}$ and $21^{st}$ of March. The first fruit of 'NECTACHIEF' (U.S. Plant Pat. No. 19,330) ripens in early July, approximately 6 days after 'ZAITABO' (BIG TOP®). More particularly, it approximately ripens between the $4^{th}$ and $13^{th}$ of July. 'MALATEWHITE' (non-patented) is a white peach variety with a good presentation and a well-balanced flavor. The maturity period begins usually in early September in the South of France climatic conditions. 'SWEETREGAL' variety has been determined to have unique tree and fruit characteristics making it worthy for commercial fresh fruit production. There are no known effects of this standard rootstock on this scion cultivar. Asexually propagated plants remained true to the original tree and all characteristics of the tree and the fruit were transmitted. The plant of the 'SWEETREGAL' variety was reproduced asexually in Elne, Pyrénées-Orientales department, France. More particularly, the plant of the 'SWEETREGAL' variety was reproduced by grafting.

SUMMARY OF THE VARIETY

The new and distinct variety of white peach tree 'SWEETREGAL' blooms in early March near Elne in the Pyrénées-Orientales department, France. The flowering period is considered as semi-late in the South of France.

The first fruit of 'SWEETREGAL' ripens in early August, around 2 weeks later than 'SWEETLOVE' (U.S. Plant Pat. No. 21,144) variety. More particularly it ripens between the $1^{st}$ of August and the $13^{th}$ of August.

DESCRIPTION OF THE DRAWINGS

In the accompanying pictures, which are as nearly true as it is reasonably possible to make in a color illustration of this type.

Figure 1:
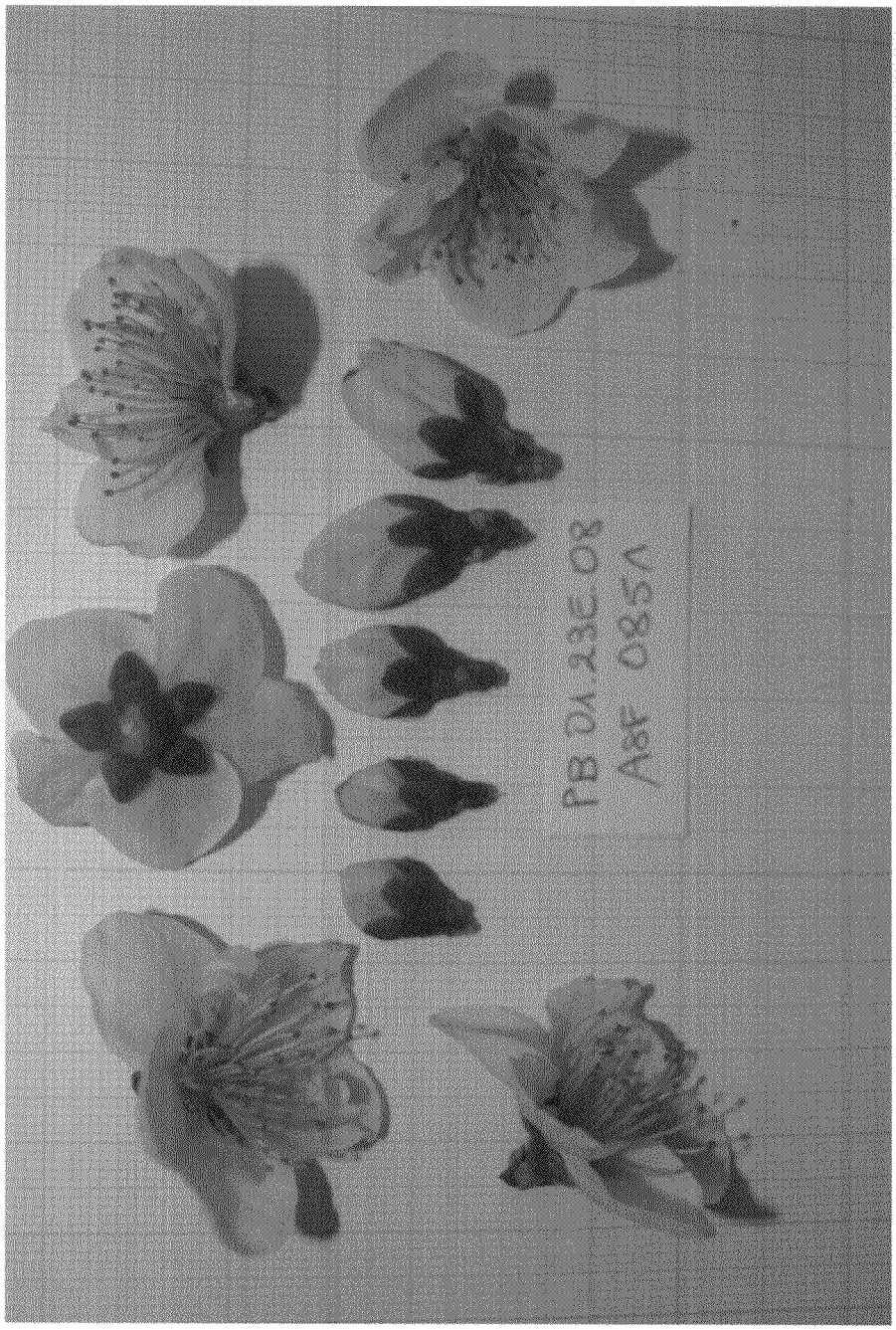
FIG. 1 is a color photograph which depicts the flower buds at different development stages, and the reverse and side view of the flower and the reproductive organs with petals removed, of the new variety.
Figure 2:
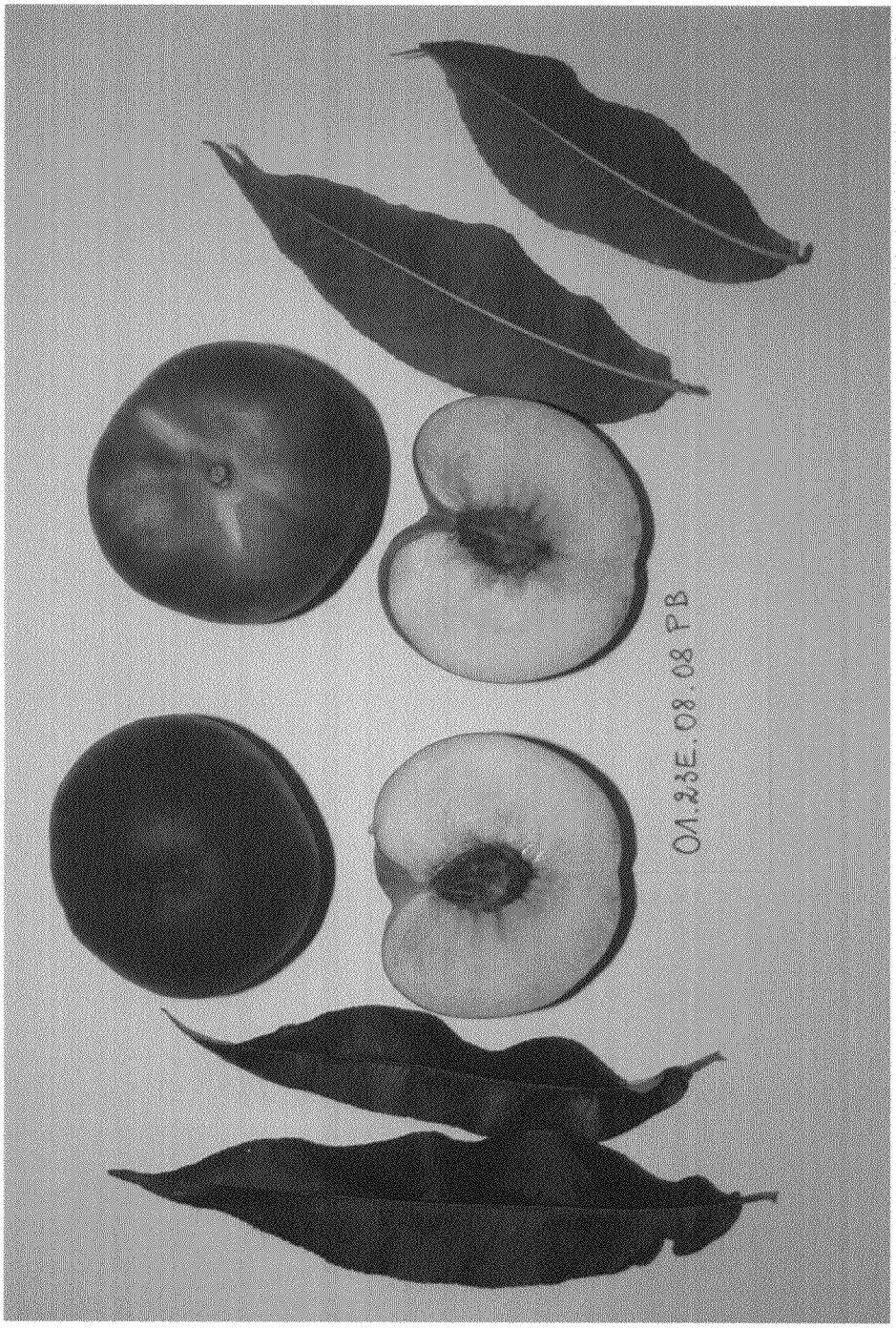
FIG. 2 is a color photograph which shows three typical specimens of the fruit, one having been cut in half with the pit being left in one of the halves for depicting fruit flesh, pit cavity and stone of the new variety.
Figure 3:
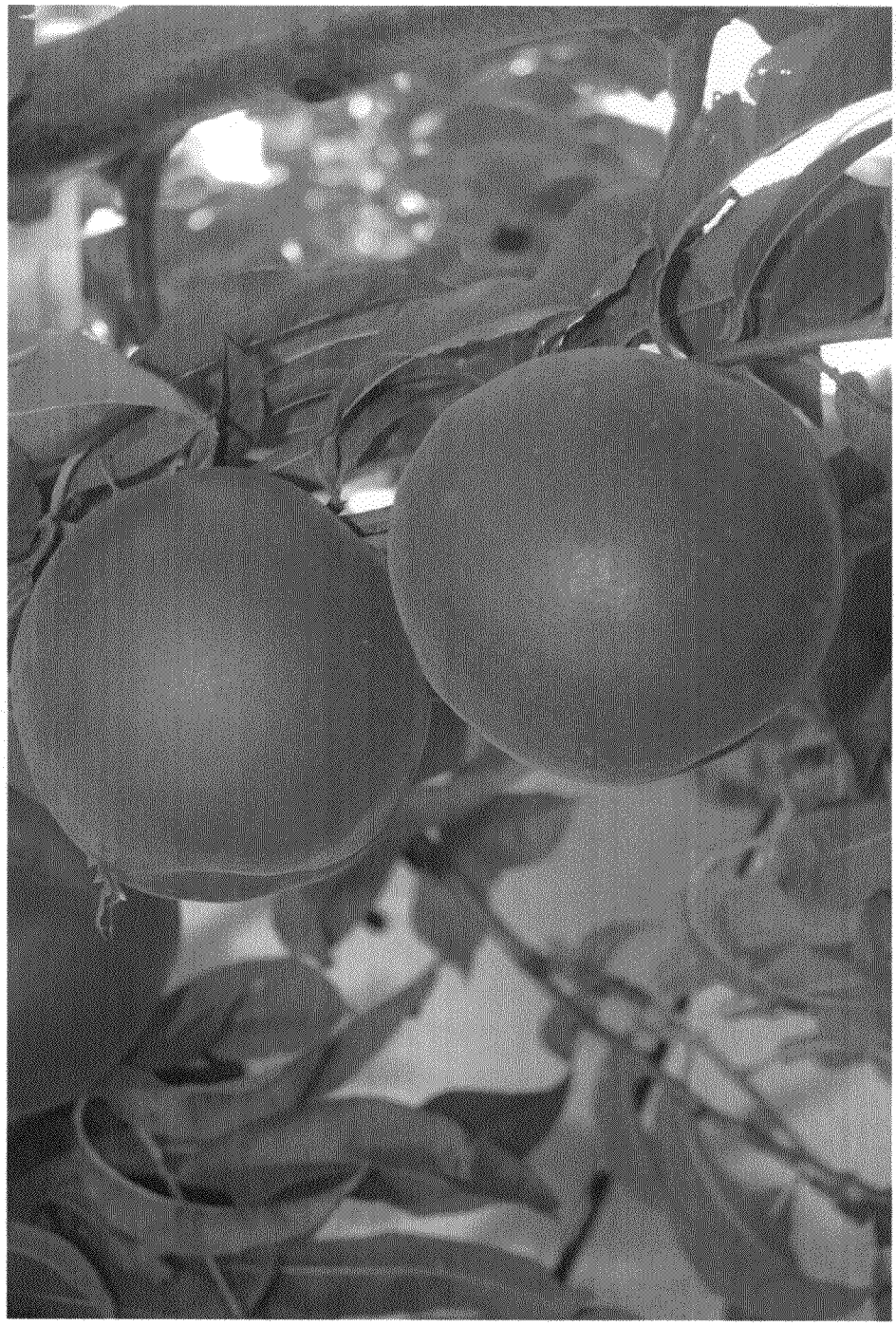
FIG. 3 is a color photograph that depicts a close view of two typical fruits on tree, at ripening time.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruit by 'SWEETREGAL' is high, due to fruit very long shelf life without alteration after harvesting.

Trees are vigorous and large stature half-standing in a semi-spread to semi-upright aspect. The flowering shoot is present excluding brushwood side away from sun. Flowering begins semi-late in springtime. The type of flower is showy, with medium to large petal size. Petals are medium pink. Leaf glands are present and reniform. Time of maturity for consumption is considered medium. The fruit flesh is white with a red pigmentation in the stone cavity. Fruit skin is very thick, of bright purple red color on a washed-pink red ground. The stone is clingstone, of small to medium size and the flesh is more or less adherent according to the maturity stage. Fruit taste is semi-sweet.

Compared to 'MASNOW' (non-patented) the blooming period is earlier of approximately 6 days. The maturity period is considered as similar but more pooled. The fruit is semi-sweet and potentially larger so the thinning must be reduced.

Compared to 'SWEETLOVE' (U.S. Plant Pat. No. 21,144) the maturity is later of 2 weeks.

DETAILED DESCRIPTION

Referring more specifically to the pomological details of this new and distinct variety of white peach tree, the following has been observed during the second fruiting season under the ecological conditions prevailing at the orchards located near the town of Elne, in the Pyrénées-Orientales department, France. All observations have been made on rootstock cultivar. The rootstock was a rootstock tree of the trademark 'FRANC INRA MONTCLAR®'. All major color code designations are by reference to The R.H.S. Colour Chart (Fourth Edition) provided by The Royal Horticultural Society of Great Britain.

Tree:

*Size*.—Medium to high as compared to other common commercial peach cultivars. The tree size the first year was approximately 2.50 meters. The tree was pruned during each following dormant season to a height of approximately 2.50 meters. Current seasons shoots growth could reach 0.80 meters. So the tree size from the second year (second and next years) reached a final height of 3.30 meters including current seasons shoots length.

*Spread*.—Approximately 1.0 meter. The whole orchard was oriented to a central leader organization, with tree lines spaced of 4.0 meters and trees spaced of 1.0 meter in a same tree line.

*Vigor*.—Strongly vigorous. The present variety grew from about 60.0 centimeters to 80.0 centimeters in height during the first and following growing seasons. For second and following seasons, the variety was pruned to an approximate height of 2.50 meters.

*Productivity*.—Very productive. Fruit set is spaced by thinning to develop the remaining fruit into the desired market sized fruit. The number of the fruit set varies with the prevailing climatic conditions and cultivar practices employed during the bloom period, and is therefore not distinctive of the present variety.

*Bearer*.—Considered very regular. A thinning of 1 fruit out of 3 was necessary for the tree valorization. Thinning may not be too important because of the high magnifying potential of the fruit.

*Form*.—Semi-spread to semi-upright naturally.

*Density*.—Considered medium dense to dense.

*Hardiness*.—The present tree was grown and evaluated in France. The variety appears to be hardy under typical central Pyrénées-Orientales department climatic conditions. Fruits remain very attractive because they are well colored with an excellent semi-sweet flavor. Experimentations on different sites with winter chilling requirement comprised between 350 hours and 1200 hours showed a good behavior of the tree in all cases. No damages were caused by ascertained temperatures as low as −12° degrees Celsius. The tree was also very resistant to frosty springtime weather.

Trunk:

*Diameter*.—Approximately between 6.0 centimeters and 7.0 centimeters when measured at a distance of approximately 30.0 centimeters above the soil, on trees from the second growing season.

*Bark texture*.—Rough, with lenticels.

*Lenticels*.—Numerous lenticels are present on trees from the second growing season. The number of lenticels reaches 3 to 5 lenticels per $cm^2$. The lenticels range in size from approximately 0.2 centimeters in height and about 0.2 to 0.5 centimeters in width.

*Lenticels color*.—The outside surface of lenticels has a silver-grey color (RHS GREY 201 C), whereas the inside surface is brown (RHS GREYED ORANGE 166 C to D).

*Bark coloration*.—The bark has a silver-grey color a little more pronounced than lenticels outside color (RHS GREY 201 C or RHS BLACK 202 C).

Branches:

*Size*.—Mature branches and current season shoots are considered medium to thick for the variety. Mature branches show a length between 70.0 and 90.0 centimeters.

*Diameter*.—Average as compared to other peach varieties. The current season shoots have a diameter from 4.0 to 10.0 millimeters, and branches of trees from the second growing season have a diameter comprised between 9.0 and 16.0 millimeters.

*Current season shoots surface texture*.—Average, wood that is several years old has no furrowed appearance.

*Crotch angles*.—Primary branches are considered variable, but the crotch angles are generally between 50 degrees and 80 degrees from the horizontal axis. This particular characteristic is not considered distinctive of the variety, however.

*Internode length*.—Generally 26.0 millimeters to 35.0 millimeters.

*Color of mature branches*.—Brown (RHS GREY BROWN 199 A to B).

*Color of current season shoots*.—The color of new shoot tips is considered a pale yellow green (RHS YELLOW GREEN 144 A to C) on lower part of new shoot tips, whereas the upper part is colored brown-purple to brown-red (RHS GREYED PURPLE GROUP 187 A to B or GREYED RED 182 A) following the position on the shoot.

Leaves:

*Size*.—Considered medium to large for the species. Leaf measurements have been taken from vigorous, upright, current-season growth at approximately mid-shoot. The ratio leaf length/leaf width is above 3.58.

*Leaf length*.—From 148.0 to 179.0 millimeters with leaf petiole. Average length of 157.0 millimeters.

*Leaf width*.—From 36.0 to 49.0 millimeters. Average width of 44.0 millimeters.

*Leaf base shape*.—Concave relative to the leaf longitudinal axis.

*Leaf form*.—Lanceolate.

*Tip form*.—Acuminate, small.

*Leaf color*.—Upper leaf surface. Dark green (RHS GREEN 137 A). Lower surface. A lighter green (RHS GREEN 137 B to C) than the upper leaf surface color. Leaf texture. Smooth and glabrous. Leaf venation. Pinnately veined.

*Mid-vein*.—Color. Light green with a yellow touch (RHS YELLOW GREEN 145 C to D) and evolves with maturity. Leaf margins. Slightly undulating. Form. Considered slightly dentate. Uniformity. Leaves are isolated or grouped by 2 or 3. In this last case, it is found one leaf of normal size with one or two smaller leaves (size-reduction of 50% and more).

*Leaf petioles*.—Size. Considered medium. Length. About 7.0 to 10.0 millimeters. Diameter. About 1.5 millimeters. Color. Light green on the upper surface (RHS YELLOW GREEN 144 A to B) and light green (RHS YELLOW GREEN 145 B) on the lower surface.

*Leaf glands*.—Size. Considered medium. Their length is about 2.0 millimeters. Their width is about 1.5 millimeter. Number. Generally 2, sometimes 2 to 4. Type. Reniform. Color. On young leaves, leaf gland color is considered pale green (RHS YELLOW GREEN 145 B). On older leaves, leaf gland color turns to a dark brown (RHS GREY BROWN 199 A to B). Margins. Smooth and regular.

*Leaf stipules*.—Generally. No leaf stipules were observed. But as seen in the characteristic relative to the leaves uniformity, it is possible to find leaves by groups of 2 or 3, with a normal-size leaf and smaller ones.

Flowers:

*Flower buds*.—Generally. At pre-floral stage of development, the floral buds are conic in form with a round tip. Their form is evolving until blooming, with variable dimensions. Just before blooming, floral buds are approximately 10.0 millimeters wide and approximately 18.0 millimeters long. Color. This characteristic is dependent upon the proximity to bloom. At pre-floral stage of development, the bottom of the flowers buds, or calyx formed by sepals, is of purple-brown color (RHS GREYED PURPLE 183 A to D or GREY BROWN GROUP 199 A); the corolla formed by petals, is generally of medium pink color (RHS RED PURPLE 65 B to C). Petals color shows an evolution until the end of blooming. Hardiness. The buds are considered hardy under typical central Pyrénées-Orientales department climatic conditions. No winter injury was noted during the last several years of evaluation in the central Pyrénées-Orientales department, with winter temperatures as low as −10° C. in January. The current variety has not been intentionally subjected to drought or heat stress, but the variety showed a very good resistance in orchard to temperatures up to 42° C. with an average temperature between 28° C. and 30° C. during 3 weeks in summer. Date of bloom. Generally early March. The first bloom was observed on Mar. 6, 2005. Second to fourth blooms took place respectively on Mar. 1, 2006, Mar. 4, 2009 and Mar. 22, 2010. Blooming time. Considered semi-late in relative comparison to other commercial peach cultivars grown in the Pyrénées-Orientales department, France. The date of full bloom is observed at the middle of the blooming period. The date of bloom varies slightly with climatic conditions and cultural practices. Duration of bloom. Approximately 7 to 9 days. This characteristic varies slightly with the prevailing climatic conditions. Flower type. The variety is considered to have a showy type flower. Flower size. Considered medium to large. Flower diameter at full bloom is approximately 30.0 to 38.0 millimeters. Bloom quantity. Considered abundant, approximately 40 flowers per meter. Flower bud frequency. Generally 2 flower buds appear per node, occasionally 1.

*Petal*.—Size. Considered medium to large for the species. Length. Generally about 17.0 millimeters. Width. Generally about 18.0 millimeters. Petal form. Round. Petal count. Nearly always 5. Petal texture. Smooth, sweet, glabrous. Petal color. Both surfaces of the petal are colored with a medium pink (RHS RED PURPLE 65 B to D) when young, darkening with advancing senescence. Fragrance. Soft.

*Petal claw*.—Form. The claw is considered to have a conic form with a slightly rounded tip. Length. Approximately 6.0 to 8.0 millimeters. Width. Approximately 4.0 to 5.0 millimeters. Petal margins. Slightly wavy, sinuate.

*Petal apex*.—Generally. The petal apices are generally complete at the tip and round.

*Flower pedicel*.—Length. Considered medium to long and having an average length of approximately 4.0 millimeters. Diameter. Average 2.0 millimeters. Color. Brown to light brown (RHS GREY BROWN N199 C to D).

*Calyx*.—Internal surface texture. Smooth and glabrous. Color. The inner surface of the calyx is considered of washed-green yellow (RHS YELLOW 13 A to B or YELLOW GREEN 150 A to B) color. The outer surface is purple brown (RHS GREYED PURPLE 183 A to D).

*Sepals*.—Number. Generally 5. Surface texture. The outer surface has a fine pubescent texture. Size.

Medium. Ovoid shape. Length. Approximately between 5.0 and 6.0 millimeters. Width. Approximately between 4.0 and 5.0 millimeters. Color. Flat red (RHS GREYED PURPLE 183 A to B). Stamens per flower. Average 40 stamens per flower.

*Anthers*.—Length. Medium. Color. Yellow orange red color (RHS YELLOW ORANGE 16 A to B). Anthers are becoming brown (RHS GREYED RED 178 A) at maturity. The color evolves with flowering. Pollen production. Pollen is abundant, and has a yellow color (RHS YELLOW ORANGE 17 B to C). The present variety is auto-fertile (self-pollinating).

*Filaments*.—Size. Variable in length, approximately 9.0 to 11.0 millimeters in length. Color. Considered pale pink (RHS RED PURPLE 62 C to D or RED PURPLE 73 A to B). The color is evolving with flowering.

*Pistil*.—Number. Usually 1. Length. Approximately from 16.0 to 18.0 millimeters including the ovary. Color. Considered very pale green (RHS YELLOW GREEN 150 D or RHS YELLOW GREEN 151 D). The color is evolving with flowering. Surface texture. Glabrous.

Fruits:

*Maturity*.—Very firm at maturity (shipping ripe).

*Date of first picking*.—Aug. 3, 2010, exceptionally late due to climatic conditions in winter 2010.

*Date of last picking*.—Aug. 13, 2010, exceptionally late due to climatic conditions in winter 2010. The date of harvest varies slightly with the prevailing climatic conditions.

*Size*.—Generally. Considered large, with a homogeneous size between them. Average cheek diameter. From 75.0 to 80.0 millimeters. Average axial diameter. From 65.0 millimeters 75.0 millimeters. Typical weight. Approximately 250.0 grams. This characteristic is highly dependent upon the prevailing cultural practices, and therefore is not particularly distinctive of the variety.

*Fruit form*.—Generally. Round to slightly oblong. The fruit is generally uniform in symmetry, viewed from pistil end. Fruit suture. Very shallow, extending from the base to the apex. No apparent callousing or stitching exists along the suture line.

*Suture*.—Color. This has generally a color similar to the blush fruit color, a bright purple red (RHS GREYED PURPLE 187 A to C) on a red ground (RHS RED 47 A to B).

*Ventral surface*.—Form. Smooth. Apex. Not prominent, sometimes very slightly marked, very small. Base. Semi-flared. Shallow. Stem cavity. Average depth of the stem cavity is about 11.0 millimeters. Average width is about 20.0 millimeters.

*Fruit skin*.—Thickness. Considered very thick and strong, and tenacious to the flesh depending on stage of maturity. Texture. Very thin and pubescent, almost glabrous. Taste. Semi-sweet, sugared, aromatic. Tendency to crack. None.

*Color*.—Blush color. This blush color is a homogenous bright purple red (RHS GREYED PURPLE 187 A to C). The red blush covers 70% to 90% of the fruit skin surface. The percentage of the blush on the fruit skin surface can vary, and is generally dependant upon the prevailing conditions under which the fruit was grown. Ground color. The ground color is washed-pink red (RHS RED 47 A to B) on 10% to 30% of the fruit. The percentage of the ground color of the fruit skin surface can vary, and is generally dependant upon the prevailing conditions under which the fruit was grown. Fruit stem. Medium in length, approximately 8.0 millimeters. Diameter. Approximately 4.0 millimeters. Color. Pale green (RHS YELLOW GREEN 145 A to B).

*Flesh*.—Ripens. Very homogenous, slow, very evenly. Texture. Very firm, very dense, crunchy, luscious, and juicy at harvesting maturity stage. Fibers. Not fibrous. Aroma. Pronounced. Eating quality. Considered very good, sweet and aromatic. Flavor. Considered semi-sweet. The Brix is generally superior to 13 degrees and acidity is comprised between 6 and 9 meq/100 ml. The flavor is considered juicy and aromatic. Juice. Very juicy at complete maturity. Brix. Superior to 13.0 degrees. This characteristic varies slightly with the number of fruit per tree; prevailing cultural practices; and the surrounding climatic conditions. Flesh color. White flesh (RHS WHITE 155 A to B or WHITE N155 D) usually with a red pigmentation (RHS RED PURPLE 61 B to C) in the stone cavity. Some pigmentation points of a red color in the fruit flesh can be observed.

*Stone*.—Type. Clingstone, more or less adherent according to the fruit maturity. Stone cavity. Medium, with an ovoid form and dimensions corresponding to the stone's dimensions. Size. Considered small to medium for the variety. The stone size varies significantly depending upon the tree vigor, crop load and prevailing growing conditions. Length. From 29.0 to 32.0 millimeters. Width. From 22.0 to 23.0 millimeters. Diameter. From 15.0 to 18.0 millimeters. Form. Elliptic. Base. Straight.

*Apex*.—Shape. The stone apex is sharp and prominent.

*Stone surface*.—Surface texture. The pit is transversely furrowed on its entire surface. Furrows are more pronounced toward the apex. The stone is pitted toward the base. Relief is prominent generally and present basally. Ridges. The surface texture is generally characterized by more prominent ridges along the ventral edges and is more prominent at the apical tip.

*Ventral edge*.—Width. Considered small to medium, and having a dimension of approximately 2.0 millimeters at mid-suture.

*Dorsal edge*.—Shape. Grooved. Stone color. The color of the dry stone is purple brown (RHS GREYED PURPLE N186 C or 187 A to B) with some zones of light brown (RHS GREYED ORANGE 174 B to C). Tendency to split. Splitting is absent or very low, depending on climatic conditions between blooming period and stone hardening.

*Kernel*.—Size. Medium. Length. About 17.0 millimeters. Width. About 12.0 millimeters. Thickness. About 5.0 millimeters. Form. Considered oblate and elliptic. Pellicle. Slightly pubescent. Color. The kernel skin is orange brown (RHS GREYED ORANGE 164 A to B or 165 B). The almond, which is the seed of the kernel, is cream-white (RHS WHITE 155 B). The kernel and its embryo are mature at the time of fruit maturity.

*Use*.—The subject variety 'SWEETREGAL' is considered to be a white peach tree of the semi-early season of maturity, and which produces fruits that are considered large, firm, and attractively colored. Fruits are excellent for uncooked consumption, crunchy or at full maturity. Due to their flesh quality, firmness and density, they can also be commercialized as $4^{th}$ range product (packed fruit or fruit in bags for example). And they are also useful for both local and very long distance shipping.

*Keeping quality*.—Excellent. Fruit stayed a little more than one week on tree before harvest and then, has stored well more than 4 weeks after harvest at 2.0 degree Celsius. They have a slow maturation and a long shelf life both on the tree after growth completion and after harvesting without alteration.

*Shipping quality*.—Considered very good. The fruit of the new peach variety showed minimal bruising of the flesh or skin damage after being subjected to normal harvesting and packing procedures. Its resistance to handling during harvest and packing and its long shelf life without alteration after harvest easily permit 3 weeks-shipping at 2° degree Celsius.

*Resistance to insects and disease*.—No particular susceptibilities were noted. The present variety is low sensitive to powdery mildew, and low sensitive to conservation diseases and decay due to its thick and strong skin.

Although the new variety of peach tree possesses the described characteristics when grown under the ecological conditions prevailing near Elne, Pyrénées-Orientales department, France, it should be understood that variations of the usual magnitude and characteristics incident to changes in growing conditions, fertilization, pruning, pest control and horticultural management are to be expected.

We claim:

1. A new and distinct variety of white peach tree as illustrated and described, characterized by a large fruit of very long shelf life without alteration after harvesting, and with a semi-sweet white flesh of high eating quality and an attractive bright purple red skin color on a washed-pink red ground.

* * * * *